United States Patent
Otsuka et al.

(10) Patent No.: US 10,386,287 B2
(45) Date of Patent: Aug. 20, 2019

(54) DROPLET SORTING DEVICE, DROPLET SORTING METHOD AND PROGRAM

(71) Applicant: Sony Corporation, Tokyo (JP)

(72) Inventors: Fumitaka Otsuka, Tokyo (JP); Masahiro Saito, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/506,497

(22) PCT Filed: Aug. 26, 2015

(86) PCT No.: PCT/JP2015/004282
§ 371 (c)(1),
(2) Date: Feb. 24, 2017

(87) PCT Pub. No.: WO2016/035284
PCT Pub. Date: Mar. 10, 2016

(65) Prior Publication Data
US 2017/0241889 A1    Aug. 24, 2017

(30) Foreign Application Priority Data
Sep. 5, 2014 (JP) .................................. 2014-181503

(51) Int. Cl.
*G01N 15/14* (2006.01)
*B01L 3/00* (2006.01)
(Continued)

(52) U.S. Cl.
CPC .... *G01N 15/1404* (2013.01); *B01L 3/502784* (2013.01); *G01N 15/14* (2013.01);
(Continued)

(58) Field of Classification Search
USPC .......................................................... 422/73
See application file for complete search history.

(56) References Cited

U.S. PATENT DOCUMENTS

| 3,710,933 A | 1/1973 | Fulwyler et al. |
| 3,826,364 A | 7/1974 | Bonner et al. |

(Continued)

FOREIGN PATENT DOCUMENTS

| CN | 1950690 A | 4/2007 |
| EP | 1403633 A2 | 3/2004 |

(Continued)

OTHER PUBLICATIONS

No Author Listed, The EPICS® ALTRA™ Flow Cytometer, Sorting Tutorial, Jul. 1, 2000, Coulter International Corporation, 47 pages.
(Continued)

*Primary Examiner* — Jill A Warden
*Assistant Examiner* — Brittany I Fisher
(74) *Attorney, Agent, or Firm* — Wolf, Greenfield & Sacks, P.C.

(57) ABSTRACT

There is provided a droplet sorting device including a detector configured to detect a state of droplets ejected from an orifice that generates a fluid stream and of satellite droplets existing between the droplets, and a controller configured to control a frequency of a driving voltage supplied to a vibration element that applies vibration to the orifice on the basis of positions where the satellite droplets exist.

12 Claims, 10 Drawing Sheets

(51) Int. Cl.
*G01N 15/10* (2006.01)
*G01N 15/00* (2006.01)

(52) U.S. Cl.
CPC ..... *G01N 15/1456* (2013.01); *G01N 15/1484* (2013.01); *B01L 2200/0652* (2013.01); *B01L 2300/0654* (2013.01); *B01L 2400/0433* (2013.01); *G01N 2015/0065* (2013.01); *G01N 2015/1006* (2013.01); *G01N 2015/1406* (2013.01); *G01N 2015/149* (2013.01); *G01N 2015/1481* (2013.01)

(56) References Cited

U.S. PATENT DOCUMENTS

| | | | |
|---|---|---|---|
| 3,924,947 A | 12/1975 | Hogg | |
| 4,009,435 A | 2/1977 | Hogg | |
| 4,168,460 A | 9/1979 | Menke | |
| 4,173,415 A | 11/1979 | Wyatt | |
| 4,284,496 A | 8/1981 | Newton | |
| 4,318,480 A * | 3/1982 | Lombardo | G01N 15/1404 209/3.1 |
| 4,318,481 A | 3/1982 | Lombardo et al. | |
| 4,325,483 A | 4/1982 | Lombardo et al. | |
| 4,350,986 A * | 9/1982 | Yamada | B41J 2/115 346/3 |
| 4,417,255 A * | 11/1983 | Furukawa | B41J 2/025 347/75 |
| 4,538,733 A | 9/1985 | Hoffman | |
| 4,616,234 A * | 10/1986 | Wint | B41J 2/115 347/80 |
| 4,987,539 A | 1/1991 | Moore et al. | |
| 5,080,770 A | 1/1992 | Culkin | |
| 5,180,065 A | 1/1993 | Touge et al. | |
| 5,483,469 A | 1/1996 | Van den Engh et al. | |
| 5,489,929 A * | 2/1996 | Vago | B41J 2/025 347/55 |
| 5,602,039 A | 2/1997 | Van den Engh | |
| 5,700,692 A | 12/1997 | Sweet | |
| 5,776,781 A | 7/1998 | Vardanega et al. | |
| 5,867,194 A * | 2/1999 | Clark | B41J 2/02 347/73 |
| 6,079,836 A | 6/2000 | Burr et al. | |
| 6,202,734 B1 | 3/2001 | Sackinger et al. | |
| 6,248,590 B1 | 6/2001 | Malachowski | |
| 6,372,506 B1 | 4/2002 | Norton | |
| 6,410,872 B2 | 6/2002 | Campbell et al. | |
| 6,589,792 B1 | 7/2003 | Malachowski | |
| 6,861,265 B1 | 3/2005 | den Engh | |
| 6,941,005 B2 * | 9/2005 | Lary | G01N 15/1425 356/317 |
| 6,949,715 B2 | 9/2005 | Kelly | |
| 7,019,293 B1 | 3/2006 | Hamada | |
| 7,024,316 B1 | 4/2006 | Ellison et al. | |
| 7,104,634 B2 * | 9/2006 | Weksler | B41J 2/09 347/19 |
| 7,159,752 B2 | 1/2007 | Farnworth | |
| 7,417,734 B2 | 8/2008 | Kanda | |
| 7,639,358 B2 | 12/2009 | Kanda | |
| 7,691,636 B2 | 4/2010 | Frazier et al. | |
| 7,723,116 B2 | 5/2010 | Evans et al. | |
| 7,758,811 B2 | 7/2010 | Durack et al. | |
| 7,880,108 B2 | 2/2011 | Schembri et al. | |
| 7,901,947 B2 | 3/2011 | Pollack et al. | |
| 8,246,805 B2 | 8/2012 | Shinoda | |
| 8,570,511 B2 | 10/2013 | Wang | |
| 8,681,335 B2 | 3/2014 | Sharpe et al. | |
| 8,691,584 B2 | 4/2014 | Durack et al. | |
| 8,748,183 B2 | 6/2014 | Durack et al. | |
| 8,883,513 B2 | 11/2014 | Pollack et al. | |
| 8,922,636 B1 | 12/2014 | Belden et al. | |
| 8,922,646 B2 | 12/2014 | Neckels et al. | |
| 9,029,724 B2 | 5/2015 | Hashimoto et al. | |
| 9,087,371 B2 | 7/2015 | Muraki | |
| 9,339,823 B2 | 5/2016 | Muraki et al. | |
| 9,429,276 B2 | 8/2016 | Katsumoto | |
| 9,588,036 B2 | 3/2017 | Shinoda | |
| 9,784,659 B2 | 10/2017 | Tanase et al. | |
| 9,784,660 B2 | 10/2017 | Otsuka et al. | |
| 9,857,286 B2 | 1/2018 | Muraki et al. | |
| 9,958,375 B2 | 5/2018 | Muraki et al. | |
| 10,132,735 B2 | 11/2018 | Muraki | |
| 2002/0171827 A1 | 11/2002 | van den Engh | |
| 2003/0222950 A1 | 12/2003 | Jeanmaire | |
| 2004/0062685 A1 * | 4/2004 | Norton | G01N 15/14 422/81 |
| 2004/0086159 A1 * | 5/2004 | Lary | G01N 15/1425 382/128 |
| 2006/0125856 A1 | 6/2006 | Kitami et al. | |
| 2006/0177348 A1 | 8/2006 | Yasuda et al. | |
| 2007/0102634 A1 | 5/2007 | Frey et al. | |
| 2007/0195310 A1 * | 8/2007 | Kanda | G01N 15/1459 356/73 |
| 2007/0257215 A1 | 11/2007 | Rich | |
| 2007/0291058 A1 * | 12/2007 | Fagerquist | B41J 2/03 347/11 |
| 2008/0024619 A1 | 1/2008 | Ono | |
| 2008/0050283 A1 | 2/2008 | Chou et al. | |
| 2008/0053205 A1 | 3/2008 | Pollack et al. | |
| 2008/0067068 A1 | 3/2008 | Li | |
| 2008/0092655 A1 | 4/2008 | Takiguchi | |
| 2008/0255705 A1 | 10/2008 | Degeal et al. | |
| 2008/0284827 A1 | 11/2008 | Fagerquist et al. | |
| 2008/0289966 A1 | 11/2008 | Voldman et al. | |
| 2009/0125242 A1 | 5/2009 | Choi et al. | |
| 2009/0170186 A1 | 7/2009 | Wu et al. | |
| 2010/0009445 A1 | 1/2010 | Patra et al. | |
| 2010/0118300 A1 | 5/2010 | Wang et al. | |
| 2010/0258195 A1 * | 10/2010 | Hawkins | F17D 1/14 137/2 |
| 2010/0258205 A1 * | 10/2010 | Hawkins | B41J 2/07 137/511 |
| 2010/0259584 A1 * | 10/2010 | Hawkins | B41J 2/07 347/74 |
| 2010/0259585 A1 * | 10/2010 | Hawkins | B41J 2/07 347/74 |
| 2010/0259586 A1 * | 10/2010 | Hawkins | B41J 2/07 347/77 |
| 2010/0315639 A1 | 12/2010 | Muraki | |
| 2011/0005931 A1 | 1/2011 | Zhe et al. | |
| 2011/0033339 A1 | 2/2011 | Muraki | |
| 2011/0081684 A1 | 4/2011 | Gauer et al. | |
| 2011/0221892 A1 | 9/2011 | Neckels et al. | |
| 2011/0259749 A1 | 10/2011 | Kanda | |
| 2011/0267457 A1 | 11/2011 | Weitz et al. | |
| 2011/0275052 A1 | 11/2011 | Schenk et al. | |
| 2011/0284378 A1 | 11/2011 | Shinoda | |
| 2011/0287976 A1 | 11/2011 | Wang et al. | |
| 2012/0076349 A1 | 3/2012 | Manri et al. | |
| 2012/0084022 A1 | 4/2012 | Giovangrandi et al. | |
| 2012/0135874 A1 | 5/2012 | Wang et al. | |
| 2012/0200857 A1 | 8/2012 | Sharpe et al. | |
| 2012/0202237 A1 * | 8/2012 | Sedoglavich | G01N 15/1404 435/29 |
| 2012/0247231 A1 | 10/2012 | Kery et al. | |
| 2012/0301869 A1 | 11/2012 | Evans | |
| 2012/0314096 A1 | 12/2012 | Kruglick | |
| 2013/0188040 A1 | 7/2013 | Kamen et al. | |
| 2013/0194589 A1 | 8/2013 | Suzuki | |
| 2013/0256136 A1 | 10/2013 | Muraki et al. | |
| 2013/0256197 A1 | 10/2013 | Katsumoto | |
| 2013/0258075 A1 | 10/2013 | Muraki et al. | |
| 2013/0286038 A1 | 10/2013 | Kamath et al. | |
| 2014/0021370 A1 * | 1/2014 | Suzuki | G01N 21/6486 250/459.1 |
| 2014/0043436 A1 | 2/2014 | Bell et al. | |
| 2014/0097129 A1 | 4/2014 | Foster et al. | |
| 2014/0144817 A1 | 5/2014 | Hashimoto et al. | |
| 2014/0174206 A1 | 6/2014 | Akiyama et al. | |
| 2014/0193059 A1 * | 7/2014 | Muraki | G01N 15/1484 382/133 |
| 2014/0212917 A1 | 7/2014 | Durack et al. | |
| 2014/0346047 A1 | 11/2014 | Shinoda | |

(56) References Cited

U.S. PATENT DOCUMENTS

| | | | |
|---|---|---|---|
| 2014/0354795 | A1 | 12/2014 | Tracy et al. |
| 2015/0068957 | A1 | 3/2015 | Otsuka et al. |
| 2015/0285726 | A1 | 10/2015 | Tanase et al. |
| 2015/0285727 | A1 | 10/2015 | Muraki |
| 2016/0148433 | A1 | 5/2016 | Petrovskaya et al. |
| 2016/0223451 | A1 | 8/2016 | Muraki et al. |
| 2016/0245736 | A1 | 8/2016 | Muraki et al. |
| 2016/0266027 | A1 | 9/2016 | Muraki et al. |
| 2017/0191925 | A1 | 7/2017 | Otsuka et al. |
| 2018/0058999 | A1 | 3/2018 | Otsuka et al. |
| 2018/0188150 | A1 | 7/2018 | Muraki et al. |
| 2018/0313740 | A1 | 11/2018 | Otsuka |

FOREIGN PATENT DOCUMENTS

| | | |
|---|---|---|
| GB | 1 103 190 A | 2/1968 |
| JP | 53-013263 | 2/1978 |
| JP | 56-030870 A | 3/1981 |
| JP | 58-187441 U1 | 12/1983 |
| JP | 62-036542 A | 2/1987 |
| JP | 62-167478 A | 7/1987 |
| JP | 64-012245 A | 1/1989 |
| JP | 09-189653 A | 7/1997 |
| JP | H09-196855 A | 7/1997 |
| JP | 10-507525 A | 7/1998 |
| JP | 11-501258 A | 2/1999 |
| JP | 2002-505423 A | 2/2002 |
| JP | 2002-521658 A | 7/2002 |
| JP | 2004-257756 A | 9/2004 |
| JP | 2005-315799 A | 11/2005 |
| JP | 2006-504970 A | 2/2006 |
| JP | 2006-242849 A | 9/2006 |
| JP | 2006-292769 A | 10/2006 |
| JP | 2007-532874 A | 11/2007 |
| JP | 2008-107110 A | 5/2008 |
| JP | 2009-145213 A | 7/2009 |
| JP | 2009-198511 A | 9/2009 |
| JP | 2009-541093 A | 11/2009 |
| JP | 2009-298012 A | 12/2009 |
| JP | 2010-510782 A | 4/2010 |
| JP | 2010-190680 A | 9/2010 |
| JP | 2010-216992 A | 9/2010 |
| JP | 2010-286292 A | 12/2010 |
| JP | 2010-286341 A | 12/2010 |
| JP | 2011-033598 A | 2/2011 |
| JP | 2011-509075 A | 3/2011 |
| JP | 2011-232033 A | 11/2011 |
| JP | 2011-237201 A | 11/2011 |
| JP | 4805417 B1 | 11/2011 |
| JP | 2012-047464 A | 3/2012 |
| JP | 2013-210264 A | 10/2013 |
| JP | 2013-210270 A | 10/2013 |
| JP | 2015-152439 A | 8/2015 |
| WO | WO 2001/002836 A1 | 1/2001 |
| WO | WO 2010/095391 A1 | 8/2010 |
| WO | WO 2010/129787 A2 | 11/2010 |
| WO | WO 2010/140460 A1 | 12/2010 |
| WO | WO 2013/145905 A1 | 10/2013 |
| WO | WO 2014/115409 A1 | 7/2014 |

OTHER PUBLICATIONS

Shapiro, HM, Chapter 6: Flow Sorting, Practical Flow Cytometry, 4th Edition, Dec. 31, 2003, pp. 257-271.
Written Opinion and English translation thereof dated Sep. 27, 2016 in connection with International Application No. PCT/JP2016/070938.
U.S. Appl. No. 13/788,075, filed Mar. 7, 2013, Muraki et al.
U.S. Appl. No. 13/788,165, filed Mar. 7, 2013, Muraki et al.
U.S. Appl. No. 14/118,788, filed Nov. 19, 2013, Muraki.
U.S. Appl. No. 14/118,994, filed Nov. 20, 2013, Hashimoto et al.
U.S. Appl. No. 14/386,368, filed Sep. 19, 2014, Otsuka et al.
U.S. Appl. No. 14/440,765, filed May 5, 2015, Tanase et al.
U.S. Appl. No. 14/737,370, filed Jun. 11, 2015, Muraki.
U.S. Appl. No. 15/028,411, filed Apr. 8, 2016, Muraki et al.
U.S. Appl. No. 15/028,419, filed Apr. 8, 2016, Muraki et al.
U.S. Appl. No. 15/093,879, filed Apr. 8, 2016, Muraki et al.
U.S. Appl. No. 15/116,830, filed Aug. 5, 2016, Otsuka et al.
U.S. Appl. No. 15/687,948, filed Aug. 28, 2017, Otsuka et al.
U.S. Appl. No. 15/907,805, filed Feb. 28, 2018, Muraki et al.
U.S. Appl. No. 15/767,426, filed Apr. 11, 2018, Otsuka.
Orme et al. "Electrostatic charging and deflection of nonconventional droplet streams formed from capillary stream breakup", Phys. Fluids., vol. 12(9); Sep. 2000, pp. 2224-2235.
International Search Report and Written Opinion received for PCT Application No. PCT/JP2015/004282, dated Nov. 6, 2015.
International Preliminary Report on Patentability and English translation thereof dated May 3, 2018 in connection with International Application No. PCT/JP2016/070938.
Hartman et al. "Jet Break Up in Electrohydrodynamic Atomization in the Cone-Jet Mode", Aerosol Sci., vol. 31(1), pp. 65-95, Mar. 1999.
Yoon et al., 3D particle position arid 3D velocity field measurement in microvolurne via the defocusing concept. Meas. Sci, Technol. 17 (2006) 2897-2905.
Morton et al., Hydrodynamic metamaterials: Microfabricated arrays to steer, refract, and focus streams of biomaterials. PNAS May 27, 2008, vol. 105(21); 7434-7438.
Luo et al., Three-dimensional tracking of fluorescent particles applied to micro-fluidic measurements. 2006. J. Micromech. Microeng. vol. 16; 1689-1699.
International Preliminary Report on Patentability dated Mar. 16, 2017 in connection with International Application No. PCT/JP2015/004282.
International Search Report and Written Opinion dated Jan. 8, 2015 in connection with International Application No. PCT/JP2014/005167.
International Preliminary Report on Patentability dated Apr. 28, 2016 in connection with International Application No. PCT/JP2014/005167.
International Search Report and Written Opinion and English translation thereof dated Nov. 18, 2014 in connection with International Application No. PCT/JP2014/074610.
International Preliminary Report on Patentability and English translation thereof dated Apr. 28, 2016 in connection with International Application No. PCT/JP2014/074610.
International Search Report and English translation thereof dated Sep. 27, 2016 in connection with International Application No. PCT/JP2016/070938.
International Search Report and Written Opinion and English translation thereof dated Feb. 24, 2015 in connection with International Application No. PCT/JP2014/080588.
Japanese Office Action and English translation thereof dated Dec. 15, 2015 in connection with Japanese Application No. 2012-080366.
Chinese Office Action and English translation thereof dated Mar. 3, 2016 in connection with Chinese Application No. 2013100954250.
International Search Report and Written Opinion dated Mar. 11, 2014 in connection with International Application No. PCT/JP2013/005910.
International Preliminary Report on Patentability dated May 21, 2015 in connection with International Application No. PCT/JP2013/005910.
Japanese Office Action dated Feb. 23, 2016 in connection with Japanese Application No. 2012-246432 and English translation thereof.
International Search Report and English translation thereof dated Mar. 12, 2013 in connection with Application No. PCT/JP2013/053324.
International Preliminary Report on Patentability and English translation thereof dated Oct. 9, 2014 in connection with Application No. PCT/JP2013/053324.
Extended European Search Report dated Aug. 26, 2014 in connection with Application No. 13768656.4.

(56) References Cited

OTHER PUBLICATIONS

International Search Report and Written Opinion and English translation thereof dated Mar. 5, 2013 in connection with Application No. PCT/JP2013/052467.

Japanese Office Action dated Jul. 15, 2014 and English translation thereof in connection with Application No. 2013-547043.

International Search Report and Written Opinion and English translation thereof dated Mar. 5, 2013 in connection with Application No. PCT/JP2013/051800.

International Search Report and Written Opinion and English translation thereof dated Jan. 21, 2014 in connection with Application No. PCT/JP2013/081152.

International Preliminary Report on Patentability and English translation thereof dated Oct. 9, 2014 in connection with Application No. PCT/JP2013/051800.

Chinese Office Action dated Aug. 25, 2015 in connection with Chinese Application No. 2013800154978 and English translation thereof.

Extended European Search Report dated Sep. 23, 2016 in connection with European Application No. 13872550.2.

International Preliminary Report on Patentability and English translation thereof dated Aug. 6, 2015 in connection with Application No. PCT/JP2013/081152.

International Preliminary Report on Patentability and English translation thereof dated Aug. 25, 2016 in connection with International Application No. PCT/JP2014/080588.

Bonner et al., Flourescence Activated Cell Sorting. Review of Scientific Instruments. Mar. 1972; 43(3):404-9.

McIntyre et all., Quantitative SLM-based differential interference contrast imaging. Optics Express. Jun. 2010; 18(13):14063-78.

Murphy et al., Differential Interference Contrast, Olympus Microscopy Resource Center, https://web.archive.org/web/20030312041453/http://www.olympusmicro.com:80/primer/techniques/dic/dichome.html, retrieved from the WayBack Machine on Mar. 30, 2018, noting date of Mar. 12, 2003, 3 pages.

Yoshimura et al., The Latest Technology [Modern Technology] of a Cell Sorter, Applied Research Report, Jasco Report. 1990;32(1):1-20.

Japanese Office Action dated Feb. 26, 2019 in connection with Japanese Application No. 2015-137487, and English translation thereof.

\* cited by examiner

[Fig. 1]
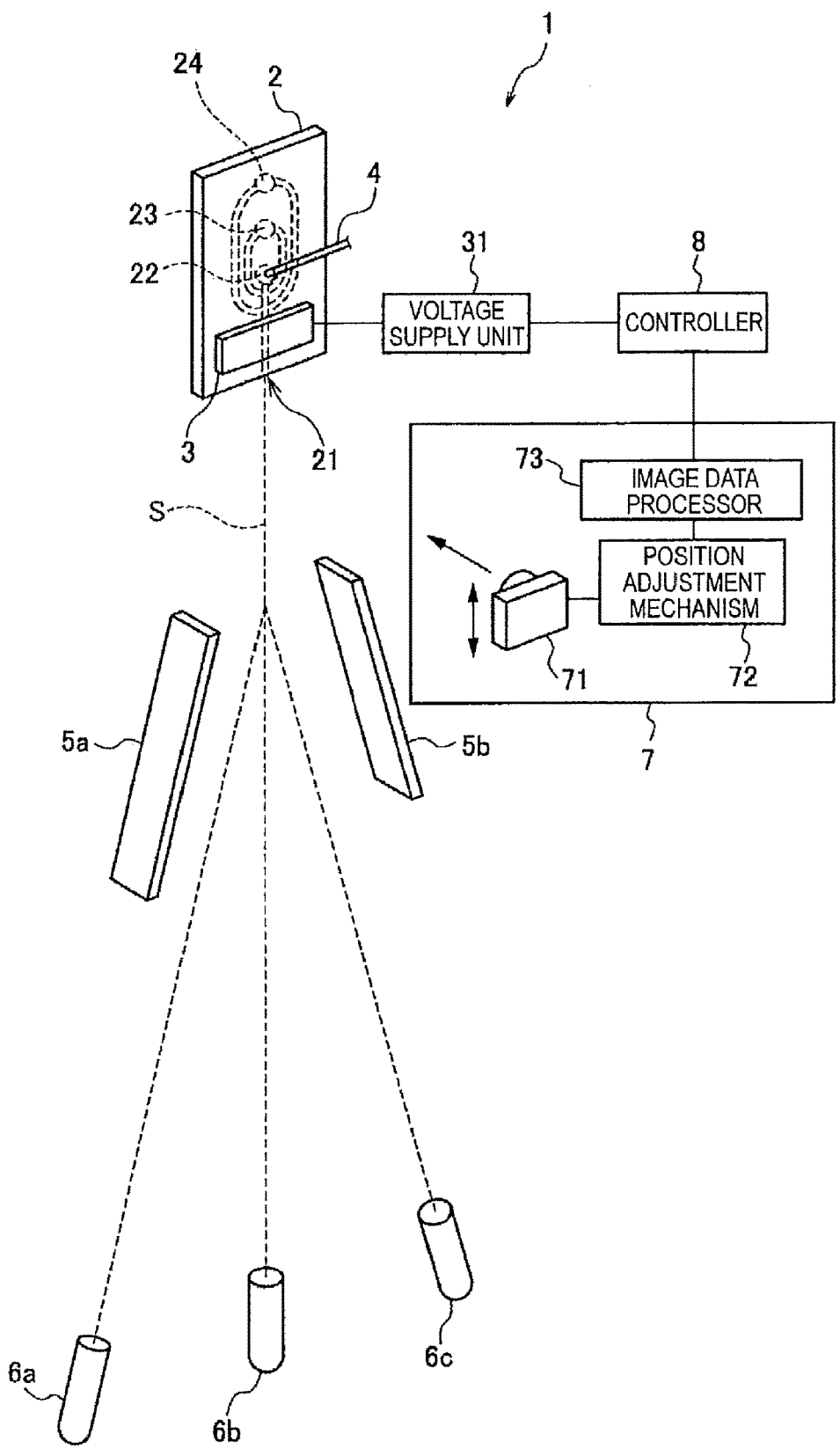

[Fig. 2A]
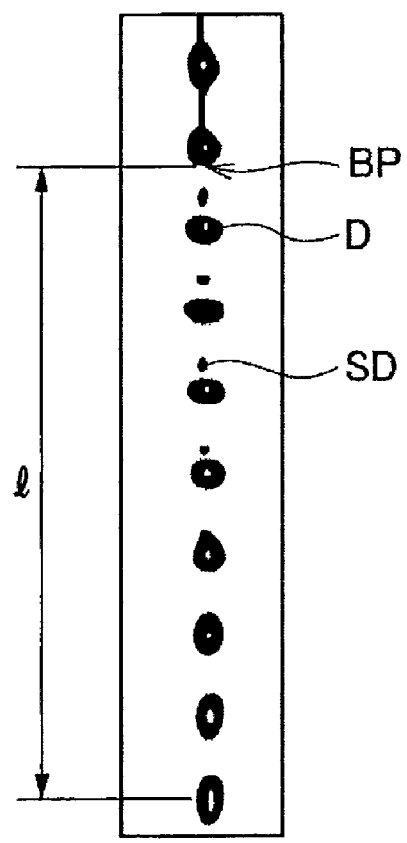

[Fig. 2B]
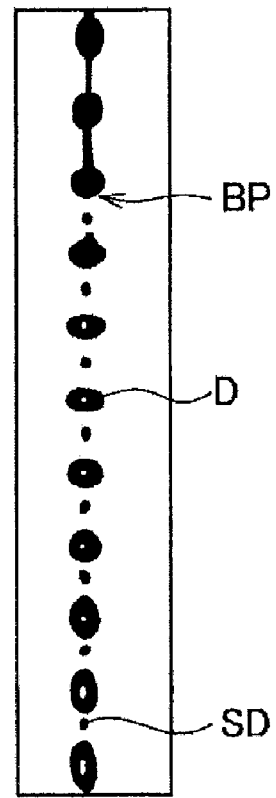
[Fig. 3A]
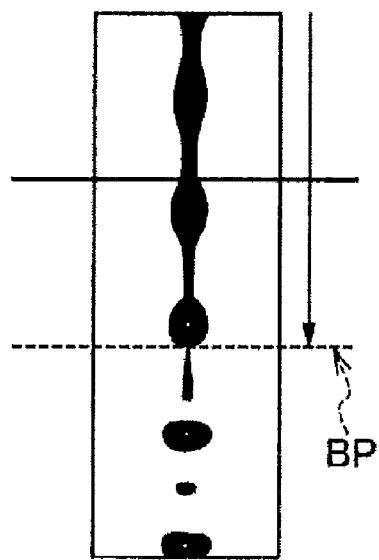

[Fig. 3B]
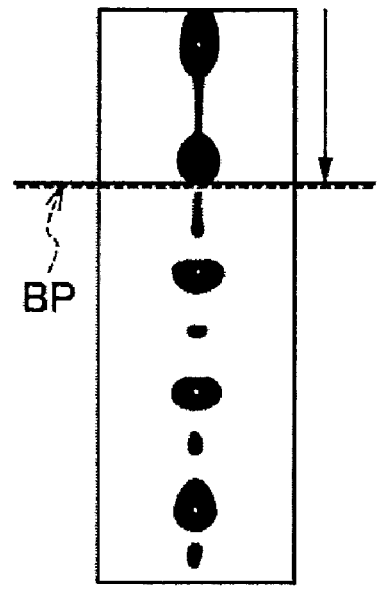
[Fig. 4A]
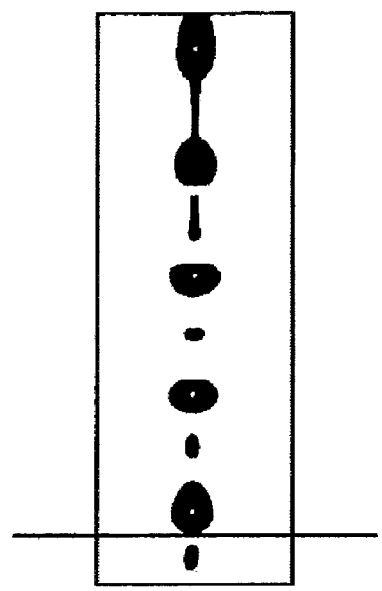

[Fig. 4B]
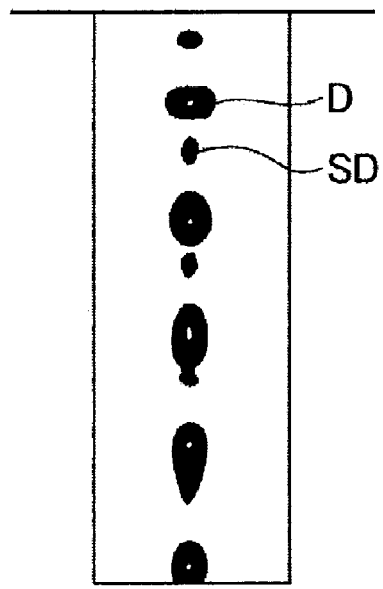
[Fig. 4C]
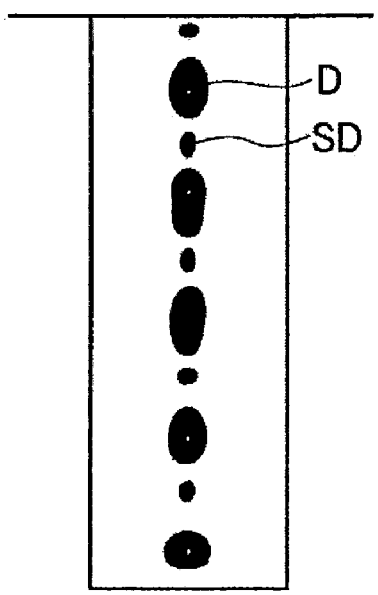

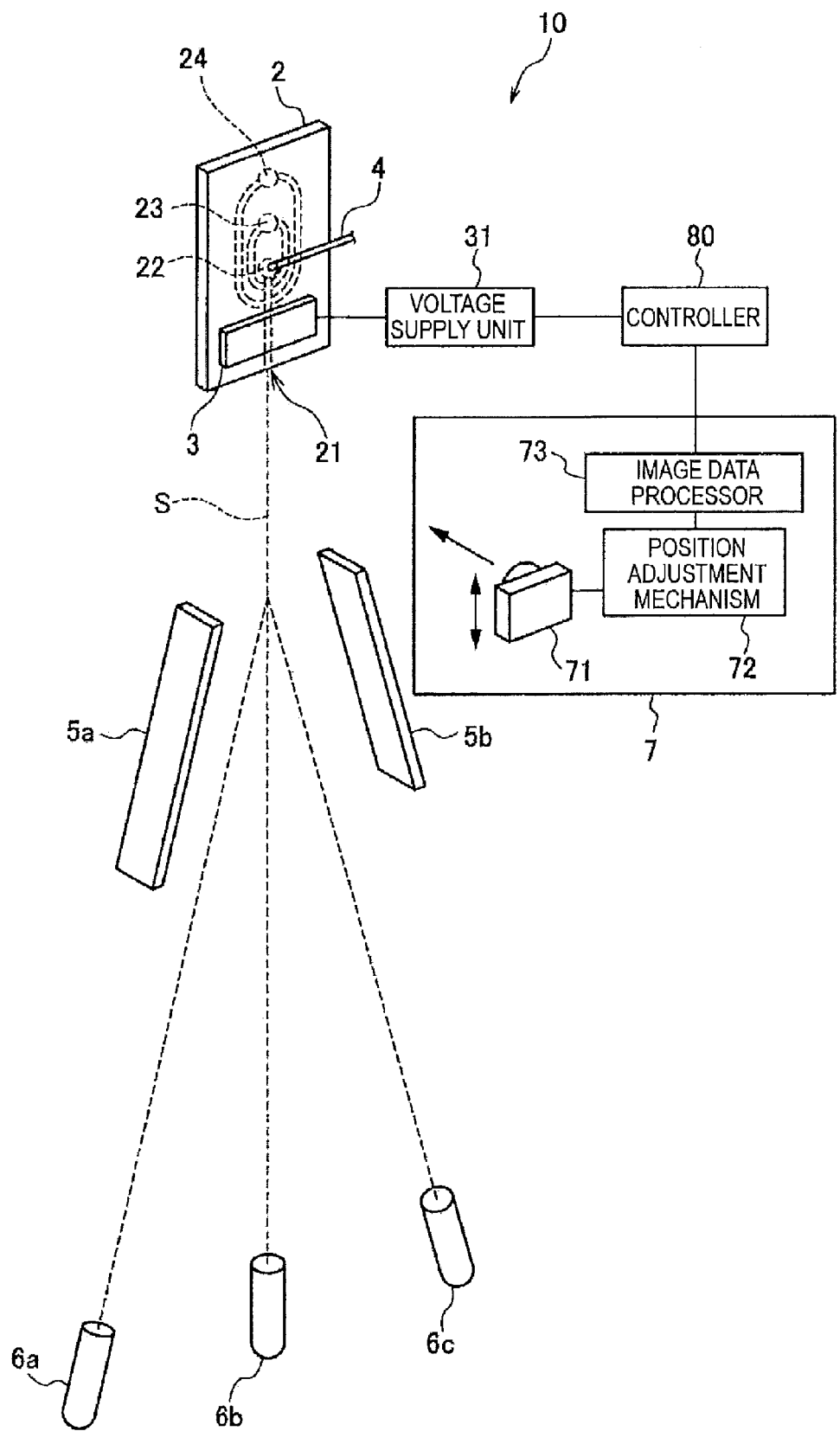
[Fig. 5]

[Fig. 6A]
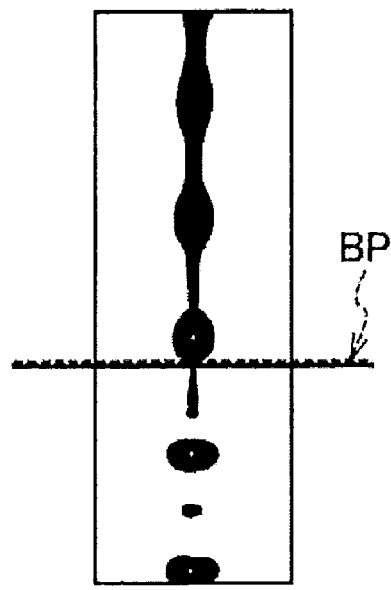
[Fig. 6B]
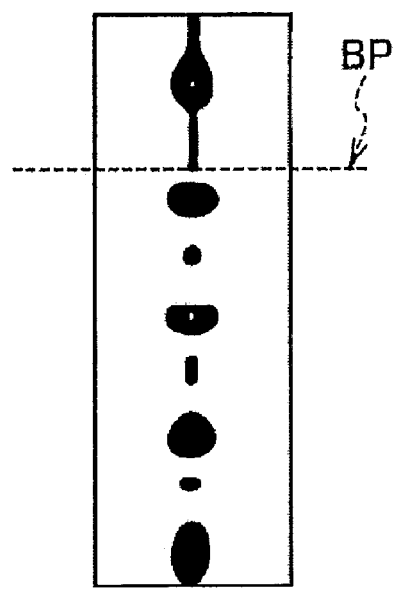

[Fig. 6C]
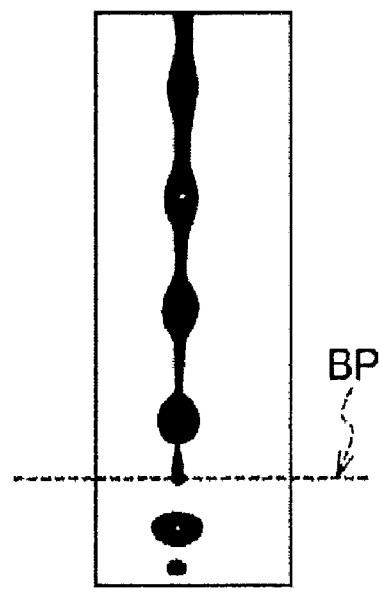

[Fig. 7]
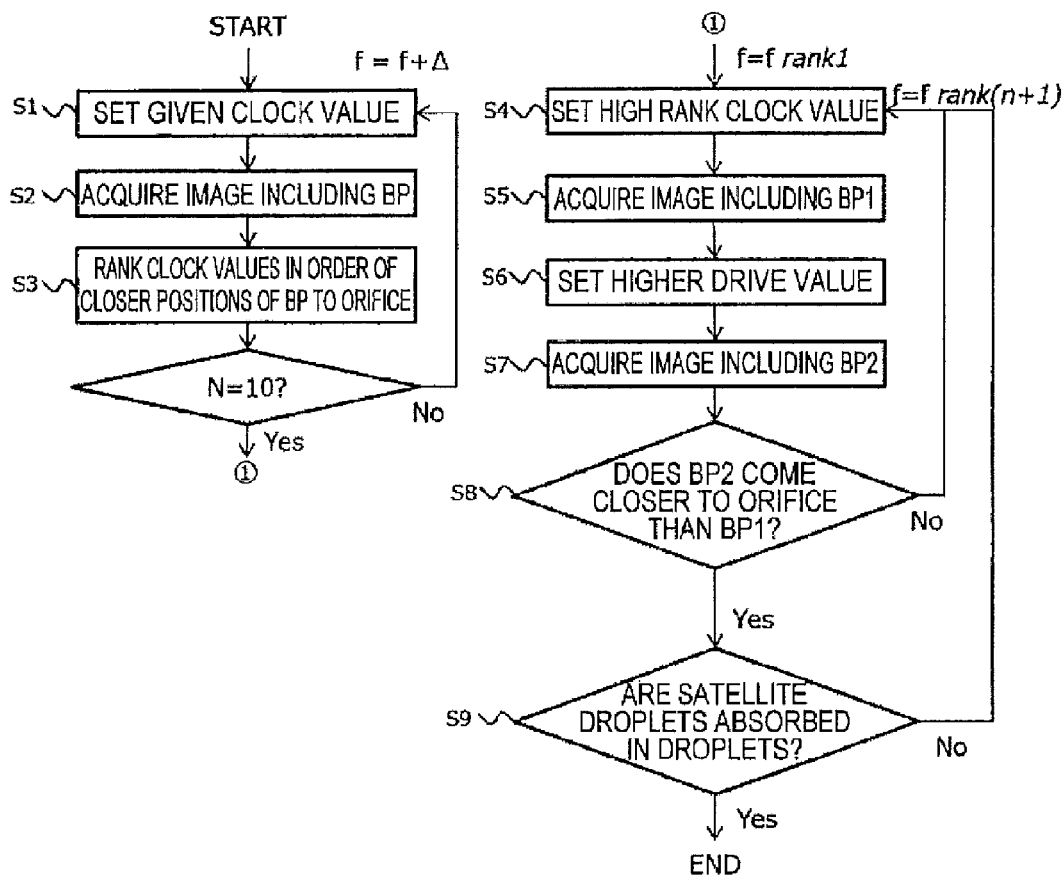

[Fig. 8]
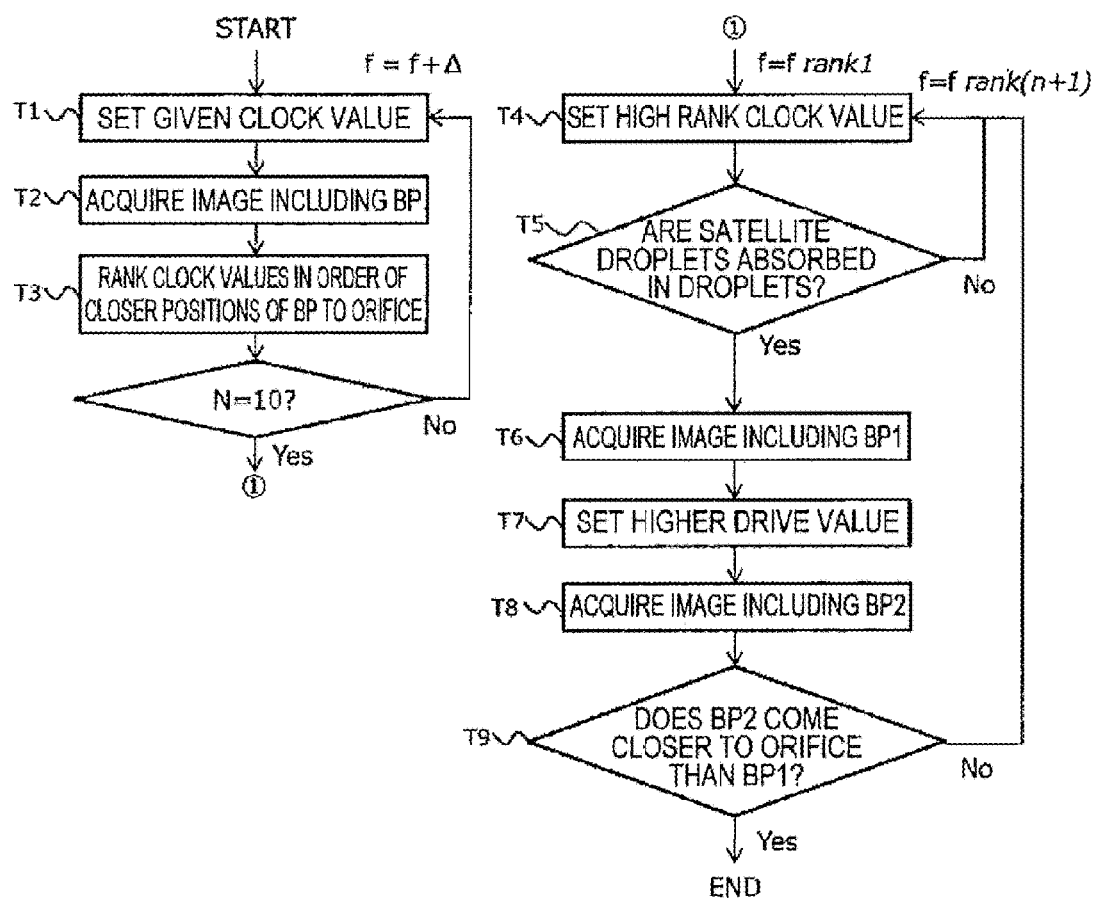

DROPLET SORTING DEVICE, DROPLET SORTING METHOD AND PROGRAM

CROSS REFERENCE TO RELATED APPLICATIONS

This Application is a national stage filing under 35 U.S.C. 371 of International Patent Application Serial No. PCT/JP2015/004282, filed Aug. 26, 2015, entitled "DROPLET SORTING DEVICE, DROPLET SORTING METHOD AND PROGRAM," which is entitled to the right of priority under 35 U.S.C. § 365(b) of Japanese application number 2014-181503, filed Sep. 5, 2014. The entire contents of these applications are incorporated herein by reference in their entirety.

TECHNICAL FIELD

The present technology relates to a droplet sorting device, a droplet sorting method and a program, and more specifically relates to a technology of separating and collecting droplets including specific particles and the like.

BACKGROUND ART

In the past, an optical measurement method using flow cytometry (flow cytometer) has been used for analyzing biologically-relevant microparticles such as cells, microorganisms and liposomes. Flow cytometers are devices to irradiate, with light, particles flowing through a flow channel formed in a flow cell, a microchip or the like, and to detect and analyze fluorescence or scattered light emitted by each of the particles.

Some flow cytometers have a function of separating and collecting only particles having specific properties on the basis of the analysis result. Particularly, such flow cytometers to sort cells are called "cell sorters." Generally, in a cell sorter, a fluid is broken into droplets upon discharged from a flow channel by causing a vibration element or the like to vibrate a flow cell or a microchip (see PTLs 1 and 2). After positively (+) or negatively (−) charged, each droplet isolated from the fluid is caused to travel in a direction deflected by deflection plates or the like, and collected in a predetermined container or the like.

However, in a droplet sorting device such as a cell sorter, sorting performance is prone to be unstable when affected by temperature change, fluid pressure fluctuation, differential pressure fluctuation occurring after sheath pressure change, and the like. Accordingly, in the past, to stabilize sorting performance, there has been proposed a microparticle sorting device configured to control a driving voltage supplied by a voltage supply unit by imaging a fluid and droplets ejected from an orifice of a flow cell or a microchip, and then by detecting the droplets from the image (see PTL 3).

CITATION LIST

Patent Literature

PTL 1: JP 2007-532874T
PTL 2: JP 2010-190680A
PTL 3: WO 2013/145905

SUMMARY

Technical Problem

Though the technology described in PTL 3 can improve the sorting performance of the droplet sorting device, there still has been demanded a still more robust droplet formation technology even less prone to be affected by environment changes.

Thus, according to an embodiment of the present disclosure, there are provided a droplet sorting device, a droplet sorting method and a program capable of stably forming droplets.

Solution to Problem

A droplet sorting device according to an embodiment of the present disclosure includes a detector configured to detect a state of droplets ejected from an orifice that generates a fluid stream and of satellite droplets existing between the droplets; and a controller configured to control a frequency of a driving voltage supplied to a vibration element that applies vibration to the orifice on the basis of positions where the satellite droplets exist.

The droplet sorting device according to an embodiment of the present disclosure can further include: an image sensor configured to acquire an image of the droplets and the satellite droplets. The detector can distinguish between the droplets and the satellite droplets on the basis of the image acquired by the image sensor.

The droplet sorting device according to an embodiment of the present disclosure may further include: a position adjustment mechanism configured to adjust a position of the image sensor.

The controller may control the frequency of the driving voltage in a manner that the satellite droplets are absorbed, within a given region from a position where a fluid discharged from the orifice is broken into droplets, in the droplets.

The image sensor may acquire an image of a position where a fluid discharged from the orifice is broken into droplets under two or more conditions of different frequencies of the driving voltage. The detector may detect a state of the satellite droplets in order from a frequency at which the fluid is broken into droplets at a position closest to the orifice.

The frequency of the driving voltage supplied to the vibration element may be controlled by detecting a state of the satellite droplets under two or more conditions of different amplitudes of the driving voltage.

The controller may control the frequency of the driving voltage in a manner that a position where a fluid discharged from the orifice is broken into droplets comes closer to the orifice as the amplitude of the driving voltage increases.

The controller may control the frequency of the driving voltage in a manner that the position where the fluid is broken into droplets comes closer to the orifice.

The detector may quantify an asymmetry of the droplets on the basis of the image. The controller may control the frequency of the driving voltage in a manner that the quantified asymmetry of the droplets falls within a predetermined range.

Another droplet sorting device according to an embodiment of the present disclosure includes: an image sensor configured to acquire an image of a fluid and droplets at a position where the fluid is broken into droplets, the fluid being discharged from an orifice that generates a fluid stream; and a controller configured to control a frequency of a driving voltage supplied to a vibration element that applies vibration to the orifice, in a manner that a position where the fluid is broken into droplets comes closer to the orifice as an amplitude of the driving voltage increases.

A droplet sorting method according to an embodiment of the present disclosure includes: detecting a state of droplets ejected from an orifice that generates a fluid stream and of satellite droplets existing between the droplets; and controlling a frequency of a driving voltage supplied to a vibration element to applies vibration to the orifice on the basis of positions where the satellite droplets exist.

A program according to an embodiment of the present disclosure causes a droplet sorting device to perform the functions of: detecting a state of droplets ejected from an orifice that generates a fluid stream and of satellite droplets existing between the droplets; and controlling a frequency of a driving voltage supplied to a vibration element that applies vibration to the orifice on the basis of positions where the satellite droplets exist.

Advantageous Effects of Invention

According to an embodiment of the present disclosure, droplets can be stably formed. Note that effects of the present disclosure is not limited to those described herein, but may be any of the effects disclosed herein.

BRIEF DESCRIPTION OF DRAWINGS

FIG. 1 shows a schematic configuration of a droplet sorting device according to a first embodiment of the present disclosure.

FIG. 2A shows a state of a fluid and droplets ejected from an orifice.

FIG. 2B shows a state of a fluid and droplets ejected from an orifice.

FIG. 3A shows a state of a fluid and droplets ejected from the orifice.

FIG. 3B shows a state of a fluid and droplets ejected from the orifice. FIG. 3B shows a state at a lower position than FIG. 3A.

FIG. 4A shows a state of a fluid and droplets ejected from the orifice.

FIG. 4B shows a state of a fluid and droplets ejected from the orifice. FIG. 4B shows a state at a lower position than FIG. 4A.

FIG. 4C shows a state of a fluid and droplets ejected from the orifice. FIG. 4C shows a state at a lower position than FIG. 4A.

FIG. 5 shows a schematic configuration of a droplet sorting device according to a second embodiment of the present disclosure.

FIG. 6A shows a droplet state before the increase of a drive value.

FIG. 6B shows a droplet state after the increase of the drive value.

FIG. 6C shows a droplet state after the increase of the drive value.

FIG. 7 is a flowchart showing an example of a control procedure of a clock value.

FIG. 8 is a flowchart showing another example of the control procedure of a clock value.

DESCRIPTION OF EMBODIMENTS

Hereinafter, modes for carrying out the present disclosure will be described in detail with reference to the attached drawings. Note that the present disclosure is not limited to the embodiments described below. The description will be given in the following order.

1. First Embodiment
(Example of a droplet sorting device configured to control a clock value on the basis of positions where satellites exit)
2. Second Embodiment
(Example of a droplet sorting device configured to control a clock value so that the break-off point can move up)
3. Modification
(Example of a droplet sorting device configured to control a clock value so that each droplet can be bilaterally symmetric)

1. First Embodiment

Firstly, description will be given of a droplet sorting device according to a first embodiment of the present disclosure. FIG. 1 shows a schematic configuration of the droplet sorting device according to the first embodiment of the present disclosure.

(Overall Device Configuration)

The droplet sorting device 1 of this embodiment, which separates and collects droplets including specified particles on the basis of an analysis result using an optical technique and the like, includes a microchip 2, a vibration element 3, a charge unit 4, deflection plates 5a and 5b, collection containers 6a to 6c and the like, as shown in FIG. 1. In addition, the droplet sorting device 1 also includes a droplet detector 7 to detect the state of satellite droplets, and a controller 8 to control the frequency of a driving voltage supplied to the vibration element 3.

(About Particles)

Particles to be analyzed and sorted by the droplet sorting device 1 of this embodiment broadly include biologically-relevant microparticles such as cells microorganisms and ribosomes, synthetic particles such as latex particles, gel particles and industrial particles, and the like.

Further, the biologically-relevant microparticles may also be the chromosomes, ribosomes, mitochondria, organelles and the like that form various types of cell. In addition, examples of cells include plant cells, animal cells, hematopoietic cells and the like. Still further, examples of microbes include bacteria such as *E. coli*, viruses such as the tobacco mosaic virus, fungi such as yeast and the like. The term biologically-relevant microparticles also includes biologically-relevant polymers such as nucleic acids, proteins, and complexes thereof.

On the other hand, examples of industrial particles include particles formed from an organic polymeric material, an inorganic material, a metal material and the like. As an organic polymeric material, polystyrene, styrene-divinylbenzene, polymethyl methacrylate and the like may be used. As an inorganic material, glass, silica, magnetic materials and the like may be used. As a metal material, for example, a metal colloid, aluminum and the like can be used. It is noted that although the shape of these microparticles is usually spherical, these microparticles may have a non-spherical shape. Further, the size, mass and the like of these microparticles is also not especially limited.

(Microchip 2)

In the microchip 2, there are formed a sample inlet 22 from which a liquid (sample fluid) including sorting target particles is introduced, a sheath inlet 23 from which a sheath fluid is introduced, a suction outlet 24 for removing clogging or air bubbles, and the like. In this microchip 2, the sample fluid is introduced from the sample inlet 22 and joins the sheath fluid introduced from the sheath inlet 23. Then, the sample fluid is sent through a sample flow channel and ejected from an orifice 21 provided to the terminal end of the sample flow channel.

The sample flow channel is connected to a suction flow channel communicating with the suction outlet 24. When clogging or air bubbles occur in the sample flow channel, this suction flow channel is used for removing the clogging or air bubbles by making the pressure inside the sample channel negative and thereby causing the fluid therein to temporarily flow backward. The suction outlet 24 is connected to a negative pressure source such as a vacuum pump.

The microchip 2 may be formed of a glass or any of various plastics (such as PP, PC, COP and PDMS). When the particles are analyzed using a technique such as an optical technique, for example, the microchip 2 is desirably formed of a material with smaller optical error due to its properties of transmissivity to measuring light, less autofluorescence and small wavelength dispersion.

The microchip 2 may be formed by wet or dry etching a glass substrate or by nanoimprinting, injection molding or machining a plastic substrate. Specifically, the microchip 2 may be formed by sealing a substrate provided with the sample flow channel and the like formed therein onto another substrate of the same or different material, for example.

(Vibration Element 3)

The vibration element 3 is either abutted on part of the microchip 2 or provided as an internal component of the microchip 2. The vibration element 3 vibrates the microchip 2 at a predetermined frequency to supply fine vibration to the sheath fluid. Thereby, the fluid (sample and sheath fluid) ejected from the orifice 21 are broken into droplets, so that a fluid stream (droplet stream) S is generated. As the vibration element 3, a piezo element or the like may be used.

(Voltage Supply Unit 31)

A voltage supply unit 31 supplies a driving voltage to the vibration element 3. The driving voltage of the vibration element 3 is supplied in a sine wave so that stable droplets may be formed, and is controlled with two parameters: frequency (clock value) and amplitude (drive value).

(Charge Unit)

The charge unit, which positively or negatively charges the droplets ejected from the orifice 21, is formed of a charge electrode 4, a voltage source configured to apply a predetermined voltage to the charge electrode 4, and the like. The charge electrode 4 is placed in contact with the sheath and/or sample fluids flowing through the flow channel so as to charge the sheath and/or sample fluids, and inserted into, for example, a charge electrode inlet of the microchip 2.

Note that, though the charge electrode 4 is placed to contact the sample fluid in FIG. 1, the present disclosure is not limited thereto. Alternatively, the charge electrode 4 may be placed to contact the sheath fluid or both the sample and sheath fluids. However, in consideration of impacts on sorting target cells, the charge electrode 4 is desirably placed to contact the sheath fluid.

By positively or negatively charging to electrify desired droplets as described above, droplets including desired particles can be isolated by electric force. Moreover, by synchronizing the charge timing of the charge unit with the voltage supplied to the vibration element 3, only the desired droplets can be selectively charged.

(Deflection Plates 5a and 5b)

The deflection plates 5a and 5b, which deflect the travel direction of each droplet in the fluid stream S by using an electric force acting on the charge applied to the droplet so as to direct the droplet into a predetermined collection container, are placed to face each other with the fluid stream S therebetween. As the deflection plates 5a and 5b, generally used electrodes may be used, for example.

Onto the deflection plates 5a and 5b, unlike voltages, that is, positive and negative voltages, are respectively applied, so that an electric field is established therebetween. When charged droplets pass through the electric field, an electric force (Coulomb force) is generated, so that each droplet is drawn toward the deflection plate 5a or 5b. In the droplet sorting device 1, the direction of each droplet stream (side stream) drawn by the electric field can be controlled by changing the polarity or the charge amount of the charge on each droplet, which enables simultaneous sorting of mutually different multiple particles.

(Collection Containers 6a to 6c)

The collection containers 6a to 6c, which collect droplets having passed between the deflection plates 5a and 5b, may be realized by using general-purpose experimental plastic tubes, glass tubes or the like. The collection containers 6a to 6c are preferably placed replaceably in the droplet sorting device 1. Among the collection containers 6a to 6c, one for receiving non-sorting target particles may be connected to a channel for draining collected droplets.

Note that the number of collection containers placed in the droplet sorting device 1 is not particularly limited. For example, when more than three collection containers are placed, it is only necessary to direct each droplet to any one of the collection containers to collect the droplet therein by using the presence or absence and the magnitude of the electric force acting on the droplet between the deflection plates 5a and 5b.

(Droplet Detector 7)

The droplet detector 7 detects the state of droplets ejected from the orifice 21 of the microchip 2 and of satellite droplets each existing between the droplets. The droplet detector 7 can be formed of components such as an image sensor 71 to image droplets and satellite droplets, a position adjustment mechanism 72 to change the position of the image sensor 71, an image data processor 73 to acquire position information of satellite droplets on the basis of an imaged image. As the image sensor 71, an imaging device such as CCD or CMOS camera, or alternatively any of various image sensors such as a photoelectric conversion element may be used. Note that, in addition to the image sensor 71, the droplet sorting device 1 of this embodiment may be provided with a light source (not shown) to illuminate an imaging region.

The image data processor 73 can be realized by an information processor formed of a general-purpose processor, main storage, auxiliary storage and the like, for example. In this case, the position information of satellite droplets can be acquired by inputting image data indicating the state of droplets and the satellite droplets imaged by the image sensor 71 to the image data processor 73, and then executing programmed control algorithm thereon. The computer program for the algorithm may be stored in a recording medium such as a magnetic disk, an optical disk, a magneto-optical disk or flash memory, or alternatively may be distributed via a network, for example.

(Controller 8)

The controller 8 controls the voltage supply unit 31, and thus controls the frequency (clock value) of the driving voltage supplied to the vibration element 3, on the basis of the position information of the satellite droplets detected by the droplet detector 7. For example, the controller 8 can be realized by an information processor formed of a general-purpose processor, main storage, auxiliary storage and the like, too.

In this case, the frequency (clock value) of the driving voltage that the voltage supply unit 31 supplies to the vibration element 3 can be automatically controlled by inputting the position information of the satellite droplets acquired by the image data processor 73 of the droplet detector 7 to the controller 8, and then executing programmed control algorithm thereon. The computer program for the algorithm may be stored in a recording medium such as a magnetic disk, an optical disk, a magneto-optical disk or flash memory, or alternatively may be distributed via a network, for example.

(Optical Detector)

When configured to analyze particles using an optical technique, the droplet sorting device 1 of this embodiment is also provided with, for example, an optical detector (not shown) to irradiate a predetermined part of the sample flow channel with light (measuring light), and to detect light (measurement target light) emitted by each microparticle flowing through the sample flow channel. The optical detector in this case may be realized similarly to that of a flow cytometry in related art. Specifically, the optical detector is realized by a laser light source, an irradiation system and a detection system. The irradiation system, which collects laser light and irradiates particles therewith, includes a condenser lens, a dichroic mirror, a bandpass filter and the like. The detection system detects measurement target light emitted by each microparticle irradiated with the laser light.

The detection system is realized by a photo multiplier tube (PMT) or an area image sensor such as a CCD or CMOS sensor, for example. Note that the irradiation system and the detection system may be provided on a single optical path, or alternatively may be provided respectively on separate optical paths. The measurement target light detected by the detecting system of the optical detector is light emitted by each particle irradiated with the measuring light, and may be scattered light such as forward or side scattered light or Rayleigh or Mie scattered light, fluorescence, or the like, for example. The measurement target light is converted into an electric signal, and the optical property of each particle is detected based on the electric signal.

(Operation)

Next, description will be given of an operation of the droplet sorting device 1 of this embodiment, that is, a droplet sorting method using the droplet sorting device 1. In the droplet sorting method of this embodiment, the following processes are performed: detecting the state of droplets D ejected from the orifice 21 and satellite droplets SD each existing between the droplets D; and controlling the frequency of the driving voltage supplied to the vibration element 3 on the basis of the positions where the satellite droplets SD exist.

Specifically, firstly, a sample fluid including sorting target particles and a sheath fluid are introduced to the sample inlet 22 and the sheath inlet 23, respectively. Then, by using, for example, the optical detector, the traveling speed (flow speed) of the particles, the time interval between two microparticles, and the like are detected as well as the optical properties of the particles. The detected optical properties, flow speed, time interval and the like of the particles are converted into electric signals, which are outputted to an overall controller (not shown) of the droplet sorting device 1.

A laminar flow of sample and sheath fluids having passed through the part, irradiated with light, of the sample flow channel is discharged from the orifice 21 to a space outside the microchip 2. At that time, the orifice 21 is vibrated by, for example, the vibration element 3, so that the discharged fluid is broken into droplets. Each of the droplets, which have been charged in the sample flow channel, is caused to travel in a direction deflected by the deflection plates 5a and 5b on the basis of a detection result by the optical detector, and thereby directed to and collected in a predetermined one of the collection containers 6a to 6c.

In this series of processes, the droplet sorting device 1 of this embodiment causes the droplet detector 7 to detect the state of droplets ejected from the orifice 21 and satellite droplets each existing between the droplets, thereby acquiring position information of the satellite droplets. On the basis of the position information of the satellite droplets, the controller 8 controls the voltage supply unit 31, thereby controlling the frequency (clock value) of the driving voltage supplied to the vibration element 3.

(Clock Value Control)

In the droplet sorting device 1 of this embodiment, in order to form droplets suitable for sorting, the vibrational frequency is automatically adjusted to a value optimal for droplet formation. Generally, the following has been known in droplet formation.

(1) The closer the break-off point to the orifice 21, the more favorable the droplets for sorting.

(2) The following states are suitable for sorting: the state (Fast) in which each satellite droplet is absorbed in the preceding droplet, and the state (Slow) in which each satellite droplet is absorbed in the following droplet.

(3) When each satellite droplet is absorbed in neither the preceding nor following droplet, side streams might sometimes be unstable.

(4) A state of a good vibration transmission property, causing the break-off point to move as the drive value changes, enables a flexible response to environment changes such as temperature change during sorting.

(5) Bilaterally symmetric droplets are suitable for sorting.

(6) In a flow-cell type (fixed) cell sorter, the vibrational frequency is previously adjusted to meet the above (1) to (5) at installation of the cell sorter, so that the user does not have to readjust the frequency at the time of using the cell sorter. However, in a chip replaceable cell sorter, since different chips necessitate a bit different frequencies to meet the above (1) to (5), it is desirable to readjust the frequency every time the chip is replaced to determine an optimal frequency for each chip.

Accordingly, by a method such as image processing, the droplet sorting device 1 of this embodiment determines a droplet formation frequency meeting the above (1) to (5), that is, a frequency (clock value) of the driving voltage of the vibration element 3. Specifically, in the droplet sorting device 1 of this embodiment, the controller 8 may control the frequency (clock value) of the driving voltage of the vibration element 3 so that, for example, each satellite droplet is absorbed in an adjacent droplet within a given region from a position (break-off point) at which the fluid discharged from the orifice 21 is broken into droplets. FIGS. 2A to 4C each show a state of the fluid and droplets ejected from the orifice 21.

For example, in the state shown in FIG. 2B, a satellite droplet SD exists in each adjacent two droplets D in the entire detected region. Accordingly, the controller 8 controls the frequency (clock value) of the driving voltage so that the satellite droplets SD are absorbed in the droplets D within the given region (length 1) from the break-off point BP, thereby allowing no satellite droplet SD to exist between the droplets D outside the distance, as shown in FIG. 2A. This can stabilize droplet formation.

Specifically, firstly, the image sensor 71 of the droplet detector 7 acquires a droplet image. In this event, as shown in FIGS. 3A and 3B, the position adjustment mechanism 72 moves the image sensor 71 so that the break-off point BP can coincide with a preset marker position (thick lines shown in FIGS. 3A and 3B), and the position of the image sensor 71 at that moment is acquired from a sensor. Thereafter, as shown in FIGS. 4A to 4C, the position adjustment mechanism 72 moves down the image sensor 71 by a certain distance so that the droplet state in a lower position can be acquired as a droplet image. Then, the image data processor 73 determines whether or not the satellite droplets SD are absorbed in the droplets D.

To determine whether an object is a droplet D or a satellite droplet SD, several methods are conceivable, and the determination method is not particularly limited. However, a method using the binarized area values of the objects or a method using the widths of the objects may be employed, for example. In the method using area values, if the area value of an object is X or more, the object is determined to be a droplet D, while if less than X, the object is determined to be a satellite droplet SD, for example. In the method using widths, the maximum of the width values of multiple objects is acquired, and if the width of an object is a half of the maximum or more, the object is determined to be a droplet D, while if less than the half, the object is determined to be a satellite droplet SD, for example. The determination can also be made by combining these two methods.

Meanwhile, it can be determined whether or not satellite droplets SD are absorbed in droplets D on the basis of the presence or absence of a satellite droplet SD below each droplet D. For example, if two successive objects are determined to be droplets D, the satellite droplet SD therebetween can be determined to be absorbed. In order to avoid determination error, satellite absorption may be determined to occur if three successive objects are determined to be droplets D.

If satellite droplets SD are determined to be absorbed, it can be further specified whether the satellite droplets SD are in the state (Fast) of being absorbed in the preceding droplets D, or in the state (Slow) of being absorbed in the following droplets D, on the basis of the position of the last detected satellite droplet SD. For example, by using this specifying method, satellite droplets SD can be determined to be absorbed only when the satellite droplets SD are in the Fast state or only when in the Slow state. This makes it possible to keep performing sorting under constant droplet condition.

By repeating the above operations while changing the frequency (clock value) of the driving voltage, the frequencies making satellite droplets SD absorbed in droplets D are selected, and an optimal frequency is determined from among the selected frequencies. Though the manner of changing the frequency (clock value) of the driving voltage is not particularly limited, the frequency can be changed in 0.1 kHz increments in the range 25 kHz plus or minus 2 kHz when the orifice 21 has a diameter of 100 micrometers, for example.

The optimal frequency (clock value) may be determined in consideration of the position of the break-off point BP. Specifically, the process of adjusting the position of the break-off point BP onto the preset marker position shown in FIGS. 3A and 3B is repeated while changing the frequency (clock value). In this case also, though the manner of changing the frequency (clock value) of the driving voltage is not particularly limited, the frequency can be changed in 0.1 kHz increments in the range 25 kHz plus or minus 2 kHz when the orifice 21 has a diameter of 100 micrometers, for example.

The position adjustment method is not particularly limited, but the position of the break-off point BP may be adjusted by a method of repeating the process of moving the image sensor 71 by a certain distance and obtaining the position of the break-off point BP at that time using image processing, for example. In another method, correlation values each between the number of pixels of a droplet image and a sensor valve of the image sensor 71 are previously obtained, and the image sensor 71 is moved so as to attain a target sensor valve calculated from a pixel distance between the break-off point BP and the marker position. This method does not necessitate imaging processing for position adjustment, thus enabling efficient position adjustment.

The frequencies are ranked in order of higher positions of the break-off point BP. It is determined whether or not satellite droplets SD are absorbed in rank order from the frequency causing the break-off point BP to be at the highest position, and a frequency (clock value) at which satellite absorption is firstly found to occur is determined as an optimal frequency. This enables more efficient frequency (clock value) adjustment.

In the above, an optimal frequency is determined by combining the frequency determination method based on the break-off point BP and the frequency determination method based on whether or not the satellite droplets SD are absorbed. This enables more efficient frequency (clock value) adjustment.

As has been described in detail, the droplet sorting device 1 of this embodiment can stably form droplets regardless of any environment change. Accordingly, an optimal droplet formation frequency can be determined for each chip in a chip replaceable cell sorter, which is thus capable of achieving highly stable and robust droplet shape control.

Moreover, the droplet sorting device of this embodiment can determine a droplet formation frequency optimal for stable side stream formation, thus being capable of achieving stable sorting. Furthermore, the droplet sorting device of this embodiment can determine a droplet formation frequency of good vibration transmission property responsive to changes of the drive value, thus being capable of achieving sorting robust against environment changes.

As a result, the droplet sorting device of this embodiment is less affected by the factors: environmental temperature change, depletion of sheath and/or sample fluids, clogging, air bubble incorporation and droplet shape change, and is thus capable of keeping achieving highly accurate and stable sorting over a long time.

Note that, in the first embodiment, description has been given of an example using the microchip 2, but the present disclosure is not limited thereto. Using a flow cell in place of the microchip 2 will provide similar effects. Similarly, the optical detector may be replaced by an electric or magnetic detector.

2. Second Embodiment

Secondly, description will be given of a droplet sorting device according to a second embodiment of the present disclosure. FIG. 5 shows a schematic configuration of the droplet sorting device according to this embodiment. Note that, in FIG. 5, components identical to those of the droplet sorting device 1 according to the first embodiment shown in FIG. 1 are denoted by the same reference numerals, and the detailed description thereof will be omitted.

(Overall Device Configuration)

Similarly to the first embodiment, the droplet sorting device 10 of this embodiment includes the microchip 2, the vibration element 3, the charge unit 4, the deflection plates 5a and 5b, the collection containers 6a to 6c, the droplet detector 7, a controller 80 and the like, as shown in FIG. 5. In the droplet sorting device 10, the frequency (clock value) of the driving voltage supplied to the vibration element 3 to vibrate the orifice 21 is controlled so that the break-off point BP comes closer to the orifice 21 as the amplitude (drive value) of the driving voltage increases.

(Controller 80)

The controller 80 controls the voltage supply unit 31, and thus controls the frequency (clock value) of the driving voltage, on the basis of the position information of the break-off point BP detected by the droplet detector 7. Specifically, the controller 80 controls the frequency (clock value) of the driving voltage supplied to the vibration element 3 so that the break-off point BP comes closer to the orifice 21 as the amplitude (drive value) of the driving voltage increases.

For example, the controller 80 can be realized by an information processor formed of a general-purpose processor, main storage, auxiliary storage and the like, too. In this case, the frequency (clock value) of the driving voltage can be automatically controlled by inputting the position information of the break-off point BP acquired by the image data processor 73 of the droplet detector 7 to the controller 80, and then executing programmed control algorithm thereon. The computer program for the algorithm may be stored in a recording medium such as a magnetic disk, an optical disk, a magneto-optical disk or flash memory, or alternatively may be distributed via a network, for example.

(Operation)

Next, description will be given of an operation of the droplet sorting device 10 of this embodiment, that is, a droplet sorting method using the droplet sorting device 10. In the droplet sorting method of this embodiment, the following processes are performed: acquiring an image of a fluid and droplets at the break-off point BP; and controlling the clock value so that the break-off point BP comes closer to the orifice 21 as the drive value increases.

(Clock Value Control)

FIG. 6A shows a droplet state before the increase of the drive value while FIGS. 6B and 6C show droplet states after the increase of the drive value. In the droplet sorting device 10 of this embodiment, firstly, the image sensor 71 of the droplet detector 7 acquires a droplet image. In this event, as shown in FIG. 6A, the position adjustment mechanism 72 moves the image sensor 71 so that the break-off point BP can coincide with a preset marker position (thick line shown in FIG. 6A).

Thereafter, the drive value is increased, and the vibration transmission property is determined on the basis of whether or not the break-off point BP moves up as the drive value increases. Specifically, if, as shown in FIG. 6B, the break-off point BP moves up from the state shown in FIG. 6A, the vibration transmission property is determined to be good, while if, as shown in FIG. 6C, the break-off point BP moves down, the vibration transmission property is determined to be poor. In this determination, the drive value may be increased by 5% in increments of 1%, for example.

Alternatively, in another method similar to this determination method by increasing the drive value, the drive value is decreased, and the vibration transmission property can be determined on the basis of whether or not the break-off point BP moves down as the drive value decreases. Note that, since the vibration transmission property is likely to be poorer as the drive value increases, the determination method by increasing the drive value will suffice for determining the vibration transmission property in the frequency (clock value) control. However, the determination may be made by combining this method and the determination method by decreasing the drive value.

By repeating these operations for multiple times while changing the frequency (clock value), the frequencies of good vibration transmission properties are selected, and an optimal frequency is determined from among the selected frequencies. In this case also, though the manner of changing the frequency (clock value) of the driving voltage is not particularly limited, the frequency can be changed in 0.1 kHz increments in the range 25 kHz plus or minus 2 kHz when the orifice 21 has a diameter of 100 micrometers, for example.

Similarly to the first embodiment, also in the droplet sorting device 10 of this embodiment, the optimal frequency (clock value) may be determined in consideration of the position of the break-off point BP. Specifically, the process of adjusting the position of the break-off point BP onto the preset marker position shown in FIG. 6A is repeated while changing the frequency (clock value).

In this case also, though the manner of changing the frequency (clock value) of the driving voltage is not particularly limited, the frequency can be changed in 0.1 kHz increments in the range 25 kHz plus or minus 2 kHz when the orifice 21 has a diameter of 100 micrometers, for example.

The frequencies are ranked in order of higher positions of the break-off point BP. It is determined whether or not satellite droplets SD are absorbed in rank order from the frequency causing the break-off point BP to be at the highest position, and a frequency (clock value) at which satellite absorption is firstly found to occur is determined as an optimal frequency. This enables more efficient frequency (clock value) adjustment.

In the above, an optimal frequency is determined by combining the frequency determination method based on the break-off point BP and the frequency determination method based on the vibration transmission property. This enables more efficient frequency (clock value) adjustment. Moreover, in the droplet sorting device 10 of this embodiment, the frequency (clock value) may be controlled by combining, with any of these frequency determination methods, the frequency determination method based on whether or not satellite droplets SD are absorbed. In this case, the frequency determination based on whether or not satellite droplets SD are absorbed may be combined with the frequency determination based on the vibration transmission property. Additionally, the frequency determination based on the break-off point BP may be combined therewith.

As has been described in detail, the droplet sorting device 10 of this embodiment can stably form droplets regardless of any environment change. Accordingly, an optimal droplet formation frequency can be determined for each chip in a chip replaceable cell sorter, which is thus capable of achieving highly stable and robust droplet shape control.

Note that the configuration and effects of the droplet sorting device of this embodiment other than those described above are similar to the first embodiment.

Additionally, the flow of the above-described embodiment will be described below in more detail. FIG. 7 is a flowchart showing an example of a control procedure of a clock value. The controller 80 sets a given frequency (clock value) as the frequency (clock value) of driving voltage in this control procedure (step S1). The controller 80 controls the droplet detector 7 to acquire an image including the break-off point BP (step S2). The controller 80 then ranks frequencies (clock values) in order of closer positions of the break-off point BP to the orifice 21 (in order of higher positions of the break-off point BP) on the basis of the above-described embodiment (step S3).

The controller 80 iteratively executes the iterative processing corresponding to steps S1 to S3 shown in FIG. 7 N times ("ten times," herein, for the sake of clarity) equal to the number of ranked pieces of data. Once the iterative processing is completed, the processing transitions to step S4.

In steps S4 to S8, the controller 80 increases drive values in rank order from the frequency causing the break-off point BP to be at the highest position on the basis of the above-described embodiment, and determines the vibration transmission property on the basis of whether or not the break-off point BP moves up as the drive value increases.

That is to say, in step S4, the controller 80 sets a high rank frequency (clock value) as the frequency (clock value) of the driving voltage. The controller 80 then controls the droplet detector 7 to acquire an image including a break-off point BP1 (step S5). Thereafter, the controller 80 controls the frequency (clock value) of the driving voltage, thereby setting a higher value as the drive value (step S6). The controller 80 then controls the droplet detector 7 to acquire an image including a break-off point BP2 (step S7). The controller 80 obtains the positions of the break-off points BP1 and BP2, and determines the vibration transmission property on the basis of whether or not the break-off point BP2 comes closer to the orifice 21 than the break-off point BP1 (step S8).

If it is not confirmed that the break-off point BP2 comes closer to the orifice 21 (NO in step S8), the processing repeats step S4. To the contrary, if it is confirmed that the break-off point BP2 comes closer to the orifice 21 (YES in step S8), the processing transitions to step S9.

In step S9, the controller 80 determines in the same method as described in the first embodiment whether or not the satellite droplets SD are absorbed in the droplets D. If the satellite droplets SD are absorbed in the droplets D (YES in step S9), the controller 80 hereby finishes controlling a clock value. To the contrary, if the satellite droplets SD are not absorbed in the droplets D (NO in step S9), the processing repeats step S4.

An example has been described in which all of the processes in steps S1 to S9 are performed in the present control procedure, but step S9 may be omitted and the processes corresponding to steps S1 to S8 alone have to be performed.

FIG. 8 is a flowchart showing another example of the control procedure of a clock value. The same processing as the above-described processing shown in FIG. 7 will not be described in detail. Steps T1 to T4 are the same as steps S1 to S4 in FIG. 7. Once the iterative processing corresponding to steps T1 to T3 is completed, steps T4 and T5 are subsequently performed in this control procedure.

In steps T4 and T5, the controller 80 determines whether or not the satellite droplets SD are absorbed in rank order from the frequency causing the break-off point BP to be at the highest position on the basis of the above-described embodiment. That is to say, in step T4, the controller 80 sets a high rank frequency (clock value) as the frequency (clock value) of the driving voltage.

Next, in step T5, the controller 80 determines in the same method as described in the above-described embodiment whether or not the satellite droplets SD are absorbed in the droplets D. If the satellite droplets SD are not absorbed in the droplets D (NO in step T5), the processing repeats step T4.

To the contrary, if the satellite droplets SD are absorbed in the droplets D (YES in step T5), the processing transitions to step T6.

In steps T6 to T9, the controller 80 increases drive values in rank order from the frequency which causes the break-off point BP to be at the highest position and at which it is determined that the satellite droplets SD are absorbed in the droplets D on the basis of the above-described embodiment, and determines the vibration transmission property on the basis of whether or not the break-off point BP moves up as the drive value increases.

That is to say, in step T6, the controller 80 controls the droplet detector 7 to acquire an image including the break-off point BP1. Thereafter, the controller 80 controls the frequency (clock value) of the driving voltage, thereby setting a higher value as the drive value (step T7). The controller 80 then controls the droplet detector 7 to acquire an image including the break-off point BP2 (step T8). The controller 80 obtains the positions of the break-off points BP1 and BP2, and determines the vibration transmission property on the basis of whether or not the break-off point BP2 comes closer to the orifice 21 than the break-off point BP1 (step T9).

If it is not confirmed that the break-off point BP2 comes closer to the orifice 21 (NO in step T9), the processing repeats step T4. To the contrary, if it is confirmed that the break-off point BP2 comes closer to the orifice 21 (YES in step T9), the controller 80 hereby finishes controlling a clock value.

An example has been described in which all of the processes in steps T1 to T9 are performed in the present control procedure, but the processes corresponding to steps T6 to T9 may be omitted and the processes corresponding to steps T1 to T5 alone have to be performed.

3. Modification

Thirdly, description will be given of a droplet sorting device according to a modification of the first and second embodiments of the present disclosure. The droplet sorting device according to this modification, an optimal frequency (clock value) is determined by additionally focusing on the bilateral symmetry of droplet shapes. Specifically, the image data processor 73 quantifies the bilateral asymmetry of droplet shapes. Then, frequencies (clock values) at which the quantified asymmetry is within a certain value are calculated. Based on these, a droplet formation frequency is determined, and the controller controls the voltage supply unit 31 to supply the driving voltage of this droplet formation frequency.

Generally, it has been known that a side stream formed of less bilaterally symmetric droplets is unstable. Accordingly, as in this modification, determining a highly bilaterally symmetric droplet formation frequency makes it possible to achieve more stable sorting.

Note that the configuration and effects of the droplet sorting device of this modification other than those described above are similar to the first or second embodiment.

Additionally, the present technology may also be configured as below.

(1)

A droplet sorting apparatus comprising a detection device configured to detect a state of a satellite droplet ejected from an orifice of a flow channel structure, and a controller configured to control a frequency of a driving voltage supplied to a vibration element based on a position of the satellite droplet, wherein the vibration element is configured to vibrate the flow channel structure.

(2)
The droplet sorting apparatus according to (1), wherein the position of the satellite droplet is a relative position to a droplet adjacent to the satellite droplet.

(3)
The droplet sorting apparatus according to (1) or (2), wherein the controller is further configured to control the frequency of the driving voltage in a manner that the satellite droplet is absorbed in the droplet within a given region from a position where a fluid discharged from the orifice is broken into the droplet and satellite droplet.

(4)
The droplet sorting apparatus according to any of (1) to (3), wherein the frequency of the driving voltage supplied to the vibration element is controlled by detecting a state of the satellite droplet under two or more conditions of different amplitudes of the driving voltage.

(5)
The droplet sorting apparatus according to any of (1) to (4), wherein the controller is further configured to control the frequency of the driving voltage in a manner that a position where a fluid discharged from the orifice is broken into a droplet and the satellite droplet moves toward the orifice as the amplitude of the driving voltage increases.

(6)
The droplet sorting apparatus according to any of (1) to (5), wherein the detection device comprises an image sensor configured to acquire an image of the droplet and the satellite droplet, and a processor configured to distinguish between the droplet and the satellite droplet based on the image acquired by the image sensor.

(7)
The droplet sorting apparatus according to (6), wherein the image sensor is arranged to acquire an image of a position where a fluid discharged from the orifice is broken into the droplet and the satellite droplet under two or more conditions of different frequencies of the driving voltage, and wherein the processor is further configured to rank the different frequencies into ranked frequencies based upon a distance between the orifice and a position at which the fluid is broken into the droplet and the satellite droplet.

(8)
The droplet sorting apparatus according to (7), wherein the controller is further configured to control the frequency of the driving voltage to step through the ranked frequencies and to vary the driving voltage to determine a first frequency for which the position where the fluid is broken into the droplet and the satellite droplet moves toward the orifice as the amplitude of the driving voltage increases.

(9)
The droplet sorting apparatus according to (9), wherein the controller is further configured to vary the frequency of the driving voltage about the first frequency to determine whether the satellite droplet is absorbed in the droplet.

(10)
The droplet sorting apparatus according to any of (6) to (9), further comprising a position adjustment mechanism configured to adjust a position of the image sensor.

(11)
The droplet sorting apparatus according to any of (6) to (10), wherein the detection device is further configured to quantify asymmetry values of the droplet based on the image, and wherein the controller is further configured to control the frequency of the driving voltage in a manner that the quantified asymmetry values fall within a predetermined range.

(12)
A droplet sorting apparatus comprising an image sensor arranged to acquire an image of a fluid ejected from an orifice at a position where the fluid is broken into droplets and satellite droplets, and a controller configured to control a frequency of a driving voltage supplied to a vibration element in a manner that a position where the fluid is broken into droplets and satellite droplets moves toward the orifice as an amplitude of the driving voltage increases, wherein the vibration element is configured to vibrate a structure that includes the orifice.

(13)
A droplet sorting method comprising detecting a state of a satellite droplet ejected from an orifice of a flow channel structure, and controlling a frequency of a driving voltage supplied to the flow channel structure based on a position of the satellite droplet.

(14)
A data storage device having machine-readable instructions that, when executed, cause a droplet sorting apparatus to perform acts of detecting a state of a satellite droplet ejected from an orifice of a flow channel structure, and controlling a frequency of a driving voltage supplied to the flow channel structure based on a position of the satellite droplet.

Note that the effects described herein are only exemplary. Accordingly, effects of the present disclosure is not limited thereto, and there may be other effects.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST 1, 10 droplet sorting device
2 microchip
3 vibration element
4 charge electrode
5a, 5b deflection plate
6a to 6c collection container
7 droplet detector
8, 80 controller
21 orifice
22 sample inlet
31 voltage supply unit
71 image sensor
72 position adjustment mechanism
73 image data processor
BP break-off point
D droplet
SD satellite droplet

The invention claimed is:
1. A droplet sorting apparatus comprising:
a detection device configured to detect a state of a satellite droplet ejected from an orifice of a flow channel structure; and
a controller configured to control a frequency of a driving voltage supplied to a vibration element based on a position of the satellite droplet, wherein the vibration element is configured to vibrate the flow channel structure, and wherein the controller is further configured to control the frequency of the driving voltage in a manner that the satellite droplet is absorbed in a droplet adjacent to the satellite droplet within a given region from a position where a fluid discharged from the orifice is broken into the droplet and the satellite droplet.

2. The droplet sorting apparatus according to claim 1, wherein the position of the satellite droplet is a relative position to the droplet adjacent to the satellite droplet.

3. The droplet sorting apparatus according to claim 2, wherein the detection device comprises:
an image sensor configured to acquire an image of the droplet and the satellite droplet; and
a processor configured to distinguish between the droplet and the satellite droplet based on the image acquired by the image sensor.

4. The droplet sorting apparatus according to claim 3, wherein the image sensor is arranged to acquire an image of a position where a fluid discharged from the orifice is broken into the droplet and the satellite droplet under two or more conditions of different frequencies of the driving voltage, and wherein the processor is further configured to rank the different frequencies into ranked frequencies based upon a distance between the orifice and a position at which the fluid is broken into the droplet and the satellite droplet.

5. The droplet sorting apparatus according to claim 3, further comprising a position adjustment mechanism configured to adjust a position of the image sensor.

6. The droplet sorting apparatus according to claim 3, wherein the detection device is further configured to quantify asymmetry values of the droplet based on the image, and wherein the controller is further configured to control the frequency of the driving voltage in a manner that the quantified asymmetry values fall within a predetermined range.

7. The droplet sorting apparatus according to claim 4, wherein the controller is further configured to control the frequency of the driving voltage to step through the ranked frequencies and to vary the driving voltage to determine a first frequency for which the position where the fluid is broken into the droplet and the satellite droplet moves toward the orifice as the amplitude of the driving voltage increases.

8. The droplet sorting apparatus according to claim 7, wherein the controller is further configured to vary the frequency of the driving voltage about the first frequency to determine whether the satellite droplet is absorbed in the droplet.

9. The droplet sorting apparatus according to claim 1, wherein the frequency of the driving voltage supplied to the vibration element is controlled by detecting a state of the satellite droplet under two or more conditions of different amplitudes of the driving voltage.

10. The droplet sorting apparatus according to claim 9, wherein the controller is further configured to control the frequency of the driving voltage in a manner that a position where a fluid discharged from the orifice is broken into a droplet and the satellite droplet moves toward the orifice as the amplitude of the driving voltage increases.

11. A droplet sorting apparatus comprising:
an image sensor arranged to acquire an image of a fluid ejected from an orifice at a position where the fluid is broken into droplets and satellite droplets; and
a controller configured to control a frequency of a driving voltage supplied to a vibration element in a manner that a position where the fluid is broken into droplets and satellite droplets moves toward the orifice as an amplitude of the driving voltage increases, wherein the vibration element is configured to vibrate a structure that includes the orifice, and wherein the controller is further configured to control the frequency of the driving voltage in a manner that a satellite droplet is absorbed in a droplet adjacent to the satellite droplet within a given region from a position where a fluid discharged from the orifice is broken into the droplets and the satellite droplets.

12. A droplet sorting method comprising:
detecting a state of a satellite droplet ejected from an orifice of a flow channel structure; and
controlling, with a controller, a frequency of a driving voltage supplied to a vibration element which is configured to vibrate the flow channel structure based on a position of the satellite droplet such that the satellite droplet is absorbed in a droplet adjacent to the satellite droplet within a given region from a position where a fluid discharged from the orifice is broken into the droplet and the satellite droplet.

* * * * *